(12) United States Patent
Deterre et al.

(10) Patent No.: US 9,364,675 B2
(45) Date of Patent: Jun. 14, 2016

(54) AUTONOMOUS INTRACORPOREAL CAPSULE WITH PIEZOELECTRIC ENERGY HARVESTING

(71) Applicant: SORIN CRM SAS, Clamart (FR)

(72) Inventors: Martin Deterre, Paris (FR); Elie Lefeuvre, Montreuil (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 13/797,018

(22) Filed: Mar. 12, 2013

(65) Prior Publication Data
US 2013/0238072 A1    Sep. 12, 2013

(30) Foreign Application Priority Data

Mar. 12, 2012 (FR) ...................... 12 52217

(51) Int. Cl.
| | | |
|---|---|---|
| A61N 1/378 | (2006.01) | |
| A61N 1/362 | (2006.01) | |
| H01L 41/113 | (2006.01) | |
| H01L 41/083 | (2006.01) | |
| H02N 2/18 | (2006.01) | |
| A61N 1/36 | (2006.01) | |
| A61N 1/375 | (2006.01) | |

(52) U.S. Cl.
CPC .............. *A61N 1/362* (2013.01); *A61N 1/3785* (2013.01); *H01L 41/0836* (2013.01); *H01L 41/113* (2013.01); *H01L 41/1134* (2013.01); *H01L 41/1138* (2013.01); *H02N 2/18* (2013.01); *A61N 1/36* (2013.01); *A61N 1/3756* (2013.01)

(58) Field of Classification Search
CPC .................................... A61N 1/3785
USPC ........................................... 607/35
See application file for complete search history.

(56) References Cited

U.S. PATENT DOCUMENTS

| | | | | |
|---|---|---|---|---|
| 3,943,936 | A * | 3/1976 | Rasor et al. | 607/35 |
| 6,919,669 | B2 * | 7/2005 | Bryant et al. | 310/366 |
| 7,729,768 | B2 * | 6/2010 | White et al. | 607/35 |
| 2006/0136004 | A1 | 6/2006 | Cowan et al. | |
| 2007/0088397 | A1 | 4/2007 | Jacobson | |
| 2007/0293904 | A1 * | 12/2007 | Gelbart et al. | 607/35 |
| 2009/0216292 | A1 | 8/2009 | Pless et al. | |
| 2010/0317978 | A1 | 12/2010 | Maile et al. | |
| 2011/0275947 | A1 | 11/2011 | Feldman et al. | |

FOREIGN PATENT DOCUMENTS

WO    WO-2007/047681 A2    4/2007

OTHER PUBLICATIONS

Changki et al., Experimental Validation of Energy Harvesting Performance for Pressure-Loaded Piezoelectric Circular Diaphragms, Smart Mater. Struct. 19 (2010) 075010, published Jun. 1, 2010, 7 pages.
Preliminary Search Report for French Patent Application No. 1252217, dated Jun. 4, 2012, 2 pages.

* cited by examiner

*Primary Examiner* — Michael Kahelin
(74) *Attorney, Agent, or Firm* — Foley & Lardner LLP

(57) ABSTRACT

An intracorporeal capsule for placement in a heart and for energy harvesting using blood pressure variations is shown and described. The capsule includes a capsule body and a piezoelectric strip coupled to a rigid surface for receiving blood pressure force. The piezoelectric strip is normally perpendicular to the direction of the force on the rigid surface. The piezoelectric strip is disconnected from the capsule body along at least two edges of the piezoelectric strip such that the blood pressure force can move the rigid surface, and thereby deform the piezoelectric strip for energy harvesting.

16 Claims, 5 Drawing Sheets

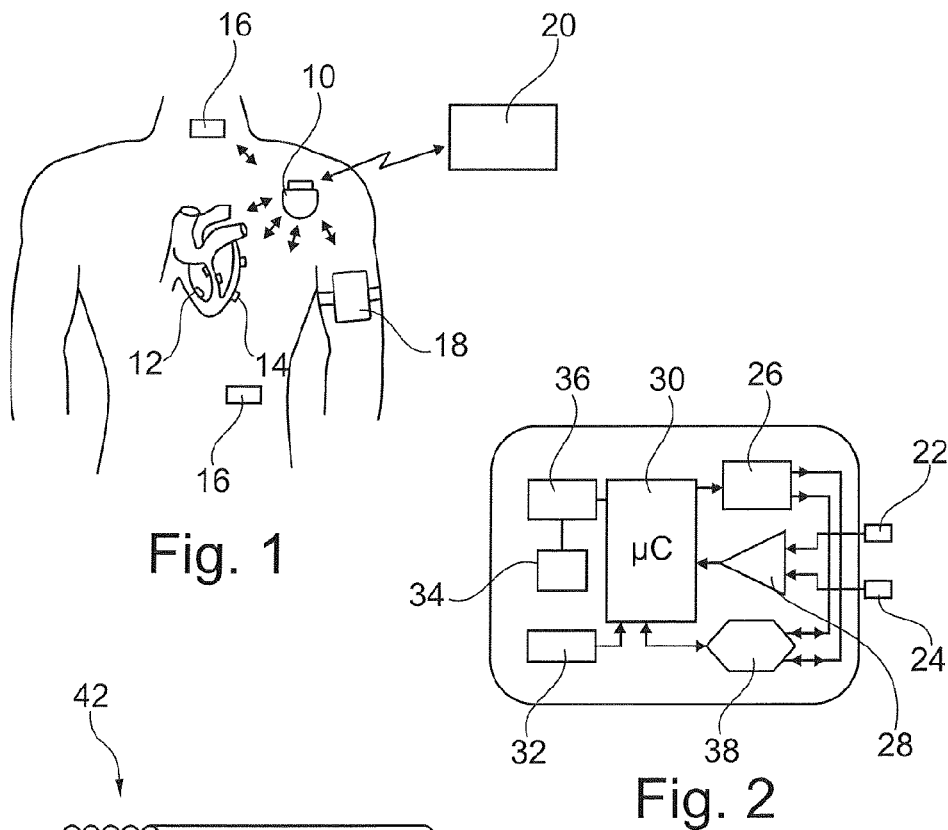
Fig. 1
Fig. 2
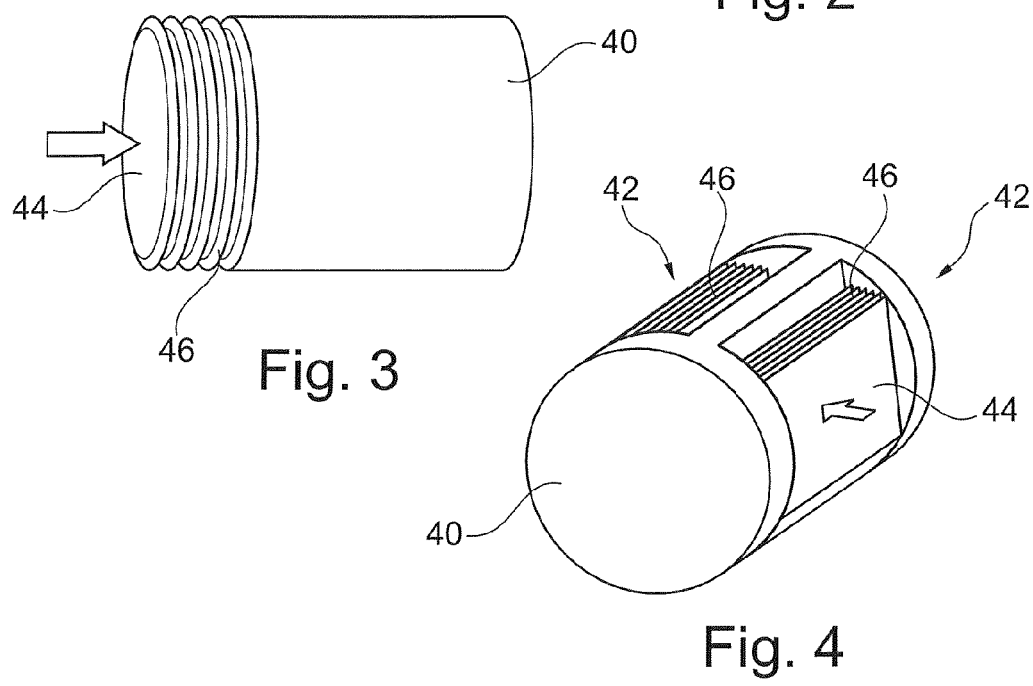
Fig. 3
Fig. 4

AUTONOMOUS INTRACORPOREAL CAPSULE WITH PIEZOELECTRIC ENERGY HARVESTING

CROSS-REFERENCE TO RELATED PATENT APPLICATIONS

The present application claims the benefit of and priority to France Priority Application 1252217, filed Mar. 12, 2012, under 35 U.S.C. §119. The entirety of France Priority Application 1252217 is incorporated herein by reference.

BACKGROUND

The present invention relates to the field of "medical devices" as may be defined, for example, by the Jun. 14, 1993 directive 93/42/CE of the European Communities. The present invention may also relate to the "active implantable medical devices" field as defined, for example, by the Jun. 20, 1990 directive 90/385/CEE of the European Communities.

Some implantable medical devices continuously monitor a patient's cardiac rhythm and, if necessary (e.g., in case of a rhythm disorder detected by the device), deliver electrical pulses to the heart for cardiac stimulation, resynchronization, cardioversion and/or defibrillation. Other implantable medical devices include neurological devices, cochlear implants, etc., as well as devices for pH measurement or devices for intracorporeal impedance measurement (such as the measure of the transpulmonary impedance or of the intracardiac impedance).

The invention relates even more particularly to those devices that implement autonomous implanted capsules which are free from any physical connection to a main implanted device (for example, main stimulation pulse generator).

These autonomous capsules are sometimes called "leadless capsules" to distinguish them from the electrodes or sensors placed at the distal end of a lead (e.g., a lead traversed throughout its length by one or more conductors galvanically connecting an electrode or a sensor to a generator).

Implants without leads (e.g., leadless capsules) are, as an example, described in U.S. 2007/0088397 A1 and WO 2007/047681 A2 (Nanostim, Inc.) or in U.S. 2006/0136004 A1 (EBR Systems, Inc.).

It is challenging and difficult to develop leadless capsules which have a long lifespan and yet remain very small and highly reliable (e.g., mechanically, electronically, bio-compatibly).

SUMMARY

One embodiment of the invention relates to an intracorporeal capsule for placement in a heart and for energy harvesting using blood pressure variations in the heart. The capsule includes a capsule body and a piezoelectric strip coupled to a rigid surface for receiving blood pressure force. The piezoelectric strip is normally perpendicular to the direction of the force on the rigid surface. The piezoelectric strip is disconnected from the capsule body along at least two edges of the piezoelectric strip such that the blood pressure force can move the rigid surface, and thereby deform the piezoelectric strip for energy harvesting.

Another embodiment of the invention relates to an intracorporeal autonomous capsule. The capsule includes a body enclosing electronic circuitry including a power supply. The capsule further includes a transducer to convert an external force applied to the capsule into electric potential. The transducer includes at least one piezoelectric strip coupled to a movable actuating member having a rigid surface which directly receives said external force and which is coupled to the piezoelectric strip. The piezoelectric strip is fixed to the body of the capsule. An energy storage and management module is powered by the deformation of the piezoelectric component due to the external force (e.g., blood pressure variations).

BRIEF DESCRIPTION OF THE DRAWINGS

FIG. 1 is a diagram of a set of medical devices including leadless capsules, implanted within the body of a patient, according to an exemplary embodiment;

FIG. 2 is a functional block diagram showing the various electronic circuits of a leadless capsule, according to an exemplary embodiment;

FIG. 3 is a perspective view of a first embodiment of the body of an implantable capsule;

FIG. 4 is a perspective view of a second embodiment of an implantable capsule body;

DETAILED DESCRIPTION

Figure 5A:
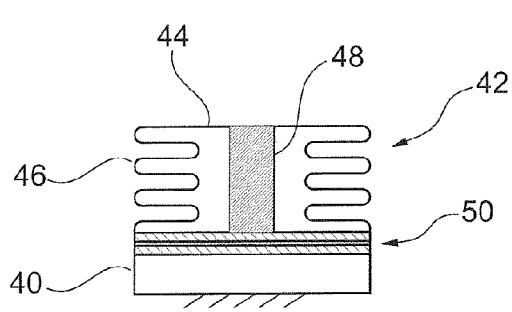
FIG. 5a is a sectional view of a piezoelectric transducer at rest of an implantable capsule, according to an exemplary embodiment.

Leadless capsules can be, for example, epicardial capsules fixed to the outer wall of the heart, or endocardial capsules, fixed to the inner wall of a ventricular or atrial cavity by a projecting anchoring screw. The anchoring screw can axially extend the capsule body and can penetrate into the cardiac tissue at the implant site. Capsules can include sensing/pacing circuits to collect myocardium depolarization potentials and/ or to apply stimulation pulses to the site where the capsule is implanted. The capsule includes one or more appropriate electrodes. Some capsules have electrodes which are formed by an active portion of the capsule's anchoring screw.

Capsules can also or alternatively incorporate one or more sensors for locally measuring the value of a parameter such as the level of oxygen in the blood, the heart intracardiac pressure, the acceleration of the heart wall, the acceleration of the patient as an indicator of activity, or other varying parameters. Leadless capsules also incorporate transmitters, receivers, or other wireless communication electronics for remotely sending and/or receiving data. It should be noted that the present application is not limited to a particular type of capsule or capsule application, unless the particular type or application is expressly recited in the claims.

The signal processing activity within the capsule and the capsule's remote transmission activity require significant energy compared to energy storage resources of small capsules. Due to its autonomous (i.e., leadless) nature, leadless capsules can only use onboard resources such as an energy harvesting circuit associated with a small integrated buffer battery. Management of the available energy on leadless autonomous capsules is challenging and difficult.

Various energy harvesting techniques have been proposed for leadless autonomous implants. For example, some energy harvesting systems today are based on an inertial device which can use the acceleration of the environment to act on a mass, known as "seismic mass", whose relative movement with respect to a piezoelectric electromagnetic or electrostatic transducer generates an electrical magnitude. The harvested power can depend on the excitation frequency, its amplitude and the utilized inertial mass. If the expected excitation frequency spectrum is centered on a fixed specific frequency, a capsule's energy harvester may be designed to resonate at the same frequency and thus benefit from a mechanical amplification to collect a maximum of the inertial energy. Capsule energy harvesters often remain limited by the excursion limits of the mass. Accordingly, conventional inertial harvesters are only powerful for stable high frequency and small amplitude applications (e.g., in the industrial domain).

In the case of the environment of the human body, the excitations used for energy harvesting at capsules come from the acceleration of the body or organs. As such, they conventionally have no specific stable frequency for which the energy harvester can be resonantly optimized. Moreover, excitation frequencies which do exist are often very low in frequency (e.g., below 10 Hz), which generate large displacements and are generally not suitable for miniaturization. Existing miniaturized generators for the human body are thus not resonantly optimized, and thus cannot generate a power density higher than that of many current batteries.

Some non-inertial devices attempt to harvest not the acceleration of the body or organs, but their movement. Some of these non-inertial devices can include mechanisms similar to that of automatic winding watches, but such mechanisms are often too large and do not provide enough power.

Another technique for energy harvesting is to harvest the pressure variations of the fluid (e.g., blood) using a flexible membrane, the deformation or movement of which can generate electricity via a transducer. Several alternative transduction methods have been proposed, such as driving a rotor, producing electromagnetic electricity like a conventional alternator. The complexity of the arrangement of parts needed for such a system largely prevents miniaturization. In addition, this type of transducer, given its magnetic nature, is not compatible with magnetic resonance imaging systems (MRIs).

Yet another proposed technique involves the harvesting of the pressure forces experienced in a heart chamber, wherein the flexible membrane drives a generator resonant at a frequency higher than the excitation frequency. The fact that the generator is resonant at a high frequency allows harvesting a large part of the mechanical energy supplied by the membrane, but the conversion rate is problematic for mechanical reliability or MRI compatibility (in the case of coupling utilizing magnets). Regarding mechanical reliability, high-frequency vibrations increase the number of cycles during a device's lifespan, which may negatively impact the mechanical reliability of the system.

In *Experimental Validation of Performance Energy Harvesting for Pressure-Loaded Piezoelectric Circular Diaphragms,* Changki et al., Smart Mater. Struct., 19 (2010), 075010, the authors propose to harvest blood pressure using a circular piezoelectric diaphragm which, by deforming, generates electrical energy. However, as the harvestable mechanical energy is proportional to the movement, a full and stiff diaphragm can not deform sufficiently under the effect of external forces such as those produced by the pressure variations, to harvest a relatively large amount of mechanical energy. In addition, the rigidity of such systems dramatically increases with reductions in size and thus miniaturization is challenging and difficult.

U.S. 2009/0216292 describes an implantable energy harvester in the form of a flexible ribbon which can be sandwiched between two adjacent layers of body tissue so as to undergo deformations with the tissue. The tissue in question may be that of a particular muscle of the pectoral region, close to the pacemaker generator to be powered through this device. Piezoelectric fibers disposed within the ribbon are deformed like the latter, resulting in the formation of electrical charges which are collected by electrodes and collected in a capacitor.

By contrast to the above systems or methods, the present application discloses an electrical power generator for an autonomous implantable capsule that is fully immersed in a body fluid that experiences regular pressure variations. Some embodiments of the present application relate to a power supply system for energy harvesting which is incorporated into an implantable capsule, the housing body of which has a member deformable under the effect of pressure changes in the environment, typically the pressure variations in the blood during the cardiac cycle. The deformation of the element is transmitted to a piezoelectric transducer, directly converting the mechanical energy of the deformation into electrical energy which is then delivered to an electrical management and storage module supplying the other electronics of the capsule with electrical energy.

The energy harvester of the present application is not sandwiched in muscle tissue, but completely immersed in a body fluid (blood) and is subject to regular pressure variations. The harvester of the invention is also mechanically engaged with only one tissue, typically the myocardial wall to which it is attached; the capsule may be retained on this wall by a flexible fastener. The capsule "floats" relatively freely in the cavity of the heart according to the movements of the blood volume. Various embodiments of the present application advantageously have one or more of the following features or benefits:

Optimum harvesting of the energy induced by the pressure variations of the body fluid;

Miniaturization: compatibility with the extremely small volume (a few cubic millimeters) of a leadless implant;

Reliability: increased reliability even over several years of life of the implant;

Insensitivity to magnetic phenomena: including MRI compatibility, which is sometimes required for implanted devices;

Not dependant on one resonant frequency;

Does not contain magnetic elements;

Biocompatibility: no external factors that may cause inflammatory reactions.

More specifically, the autonomous intracorporeal capsule includes a transducer of energy harvesting and an energy storage and management module. The energy harvesting transducer converts an external physical force applied to the capsule into electrical potential. The transducer includes at least one piezoelectric component coupled to a movable actuator receiving said external physical force. The piezoelectric component includes at least one structure with at least one piezoelectric strip fixed to the body of the capsule at one end and subjected to an external physical force at a point of application (e.g., located at another end). The storage and power management module is powered by the energy harvesting transducer under the effect of deformation of the piezoelectric component due to the external physical force received and provided to the piezoelectric component by the movable actuator. The movable actuator may include a rigid surface coupled to the piezoelectric component and a resiliently deformable bellows (i.e., flexible membrane, elastic surround, flexible sides, etc.) connecting the rigid surface to the rest of the body.

One embodiment of the invention relates to an intracorporeal autonomous capsule including an energy harvester. The energy harvester has a movable actuator that can deform and/or move relative to the fixed rigid body of the capsule. When the capsule is placed in a cardiac chamber or blood medium, blood pressure will be applied on the body and on the movable actuator. Due to pressure changes during the cardiac cycle, the movable actuator of the capsule is subject to varying forces over time, and, in view of its flexibility, deforms or moves according to the pressure variation cycle, thus reliably storing mechanical energy. This mechanical energy is converted into electricity by a piezoelectric transducer secured at one location to a fixed part of the body, and secured at another location to the movable actuator. The transducer itself may also be subject to mechanical deformation that converts electrical energy by direct piezoelectric effect. The piezoelectric transducer can operate in a non-resonant mode at the same frequency as the external pressure variations. Advantageously, the piezoelectric transducer is thus not subject to the constraints of frequency conversion involving the presence of a seismic mass.

The piezoelectric component may be structured in a strip or strips to reduce its stiffness and increase its deformation for improved energy harvesting. The structure may further be a long thin strip, forming a beam fixed at one end and free (for movement) at the other end (e.g., the end subjected to external stress).

Embodiments of the present invention include arrangements of the strips which advantageously increase the length of the strip structure of the piezoelectric component while maintaining a small surface. For example, in some embodiments the piezoelectric strip may be spirally wound, formed of folded rectilinear segments, or have an annular structure.

The piezoelectric component may advantageously include two parallel piezoelectric strips positioned around a common point of application. The capsule may include a plurality of piezoelectric members arranged in series or in parallel.

The present application includes several possible embodiments related to the movable actuator. According to one embodiment, the movable actuator includes a rigid surface coupled to the piezoelectric component and an elastically deformable member connecting the rigid surface to the rest of the capsule body. The elastically deformable connection may be formed by a bellows or by peripheral corrugations in a flexible material around the rigid surface. In another embodiment, the movable actuator includes a stretchable membrane coupled to the piezoelectric component.

With reference to FIGS. 1 to 17b, various embodiments of an energy harvester transducer and related medical devices, e.g., capsules, are shown and described.

Referring now to FIG. 1, a set of medical devices implanted within the body of a patient is shown, according to an exemplary embodiment. The set of medical devices may include an implant 10, such as an implantable defibrillator, pacemaker, resynchronizer, subcutaneous defibrillator, or event recorder. This device 10 is the master device of a network including one or more of a plurality of slave devices 12 to 18. The slave devices may include intracardiac 12 or epicardial 14 capsules implanted directly on the patient's heart, other devices 16 such as myopotential sensors or neurological stimulation devices, and optionally an external device 18 arranged on a cuff and provided with electrodes in contact with the skin. The device 10 can also be used as a gateway to the outside world by communicating with an external device 20 (e.g., a controller or remote data device with which they can communicate via telemetry).

FIG. 2 schematically illustrates the internal circuit of the implantable autonomous capsules 12 to 16.

The capsule of FIG. 2 includes a pair of electrodes 22, 24 connected to a circuit 26 for generating stimulation pulses (for an active capsule incorporating this function) and/or to a detection circuit 28 for the collection of depolarization potential collected between the electrodes 22 and 24. A core circuit 30 includes the electronics used to control the various functions of the capsule including, for example, the storage of the collected signals. The core circuit 30 may be or include a microcontroller and an oscillator generating the clock signals for the operation of the microcontroller and for communication electronics. The core circuit 30 may also contain an analog/digital converter and a digital storage memory. The capsule may also be provided with a sensor 32 such as an acceleration sensor, a pressure sensor, an hemodynamic sensor, a temperature sensor, an oxygen saturation sensor, or another type of sensor. The capsule includes a harvesting stage 34 (i.e., energy harvester, energy harvesting module, energy harvesting device, etc.) for power supply of circuitry through a power management stage 36. The electrodes 22 and 24 are also connected to a pulse transmission and/or reception circuit 38 for wireless communication with the master device or the other capsules. The energy harvesting stage 34 may use the pressure variations in the environment, in particular the cyclic variations of blood pressure, to deform a piezoelectric material. Energy harvesting is achieved by the creation of electrical charges resulting from the mechanical strain applied to the piezoelectric material under the effect of changes in blood pressure.

To take into account these deformations, the capsule may be formed as a body 40 provided, as shown in FIGS. 3 and 4, with one or more deformable elements 42. The deformable elements 42 operate at the rate of change in the pressure of the fluid that surrounds the capsule (e.g., changes in blood pressure, in the case of a cardiac capsule). The deformable element 42 is shown to include a rigid surface 44 on which pressure is applied, and which is connected to the body by a bellows 46 deformable under the effect of the external stress to which the rigid surface 44 is subjected.

In the example of FIG. 3, the rigid surface 44 or bellows 46 is arranged on an axial end side of the body 40 of the capsule, which has a generally cylindrical shape. The capsule dimensions may be of the order of 6 mm for the diameter and a length of 20 mm. The capsule may have a small volume of about 0.5 cm$^3$.

In the example of FIG. 4, two deformable sets of elements are 42 arranged on lateral sides of the body 40 of the capsule are provided. The rigid surfaces 44 are connected to the block 40 by the bellows 46. The rigid surfaces 44 are parallel to each other and to the main axis of the capsule. This configuration allows splitting the energy harvesting system; it also frees both axial ends of the capsule, which may be used to place an anchoring screw system (and the ends are not obscured by the energy harvester).

The body 40 with its deformable elements 42 may advantageously be made as a single piece (e.g., of titanium evaporated or electrodeposited on a soluble stylet).

Figure 5B:
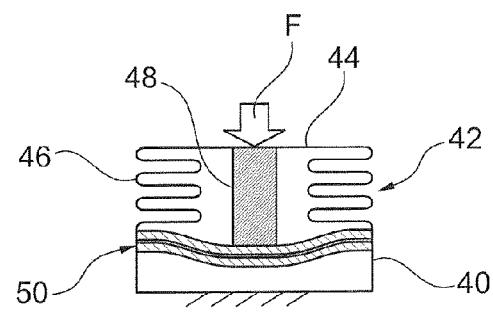
FIG. 5b is a view of the transducer of FIG. 5a in operation, according to an exemplary embodiment.
Figure 5C:
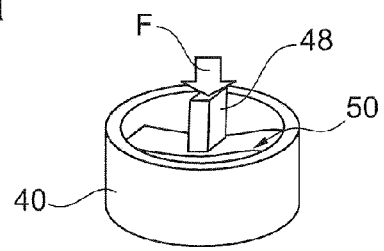
FIG. 5c is a partial perspective view of the transducer of FIGS. 5a and 5b, according to an exemplary embodiment.

Referring now to FIGS. 5a-5c, the external blood pressure physical strain F, applied to the rigid surface 44, is transmitted via a connection pin 48 to a piezoelectric energy harvesting transducer 50, for conversion of this mechanical stress F into electrical charges through the direct piezoelectric effect in which the created mechanical stress generates electrical charges to the terminals of electrodes deposited in the transducer 50 on both sides of a piezoelectric material. The electrical energy thus collected is then processed by the storage and power management module 36.

Generally, the mechanical energy at the input is due to the blood pressure, i.e. tens to hundreds of mN for a large displacement. Accordingly, the stiffness of the system may be small, typically a few hundred to a few thousand mN/m. This kind of stiffness is challenging and difficult to achieve with standard piezoelectric elements (e.g., a circular element which spans the entirety of a circular gap).

Figure 9A:
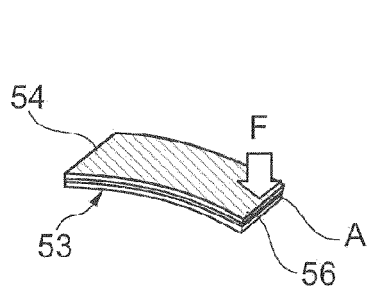
FIGS. 9a to 9c are perspective views of different structures of straight piezoelectric strips, according to an exemplary embodiment.

To meet these criteria of flexibility and dimensions, while remaining compatible with the requirement of miniaturization, it is proposed that the components constituting the piezoelectric transducers used in energy capsules according to the invention have a structure or and/or including at least one strip, such as the strip 53 of FIG. 9a. As shown in FIG. 9a, strip 53 is a thin and long beam slotted or fixed at one end 54 to the body 40 of the capsule and subjected to the external force F at an application point A located at another end 56. The strip or strips are, in some embodiments, a few millimeters in length, a few hundred micrometers in width and are tens to hundreds of micrometers thick.

Figure 11A:
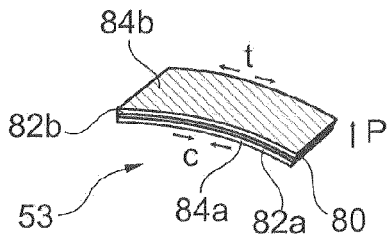
FIGS. 11a to 11c are perspective views of different electrode structures for bimorph piezoelectric strips, according to an exemplary embodiment.
Figure 12A:
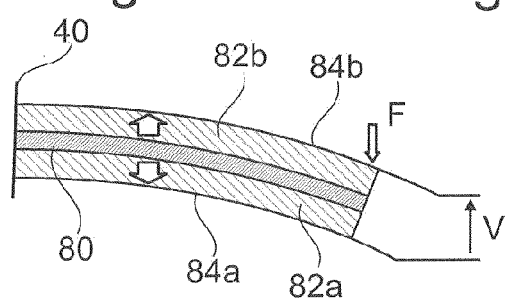
FIGS. 12a and 12b are sectional views respectively showing serial and parallel configurations of electrodes of the structure of FIG. 11a, according to an exemplary embodiment.
Figure 12B:
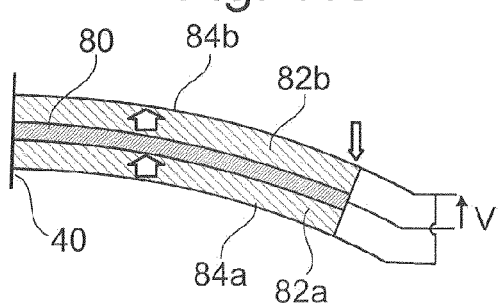

As can be seen in FIG. 11a, the strip 53 has a bimorph electrical structure with two piezoelectric layers 82a, 82b arranged on both sides of a substrate 80 and two electrodes 84a, 84b completely covering the piezoelectric layers. In this case, the component is biased along the thickness of the strip 53 for harvesting in a mode wherein the polarization P is perpendicular to the direction of the stress, namely fraction T on the upper layer 82b and the compression C on the lower layer 82a. In addition, as shown in FIGS. 12a and 12b, the electrodes 84a, 84b may be connected in series (FIG. 12a) or in parallel (FIG. 12b).

The piezoelectric layers 82a, 82b may be made of a material such as PZT ceramics or PMN-PT monocrystals, barium titanate, or lithium niobate with a high electromechanical coupling.

Figure 11B:
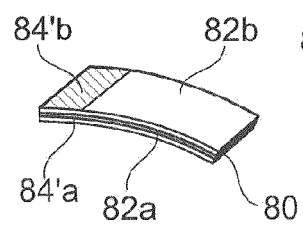

In FIG. 11b, the electrodes 84'a, 84'b only partially cover the piezoelectric layers 82a, 82b, wherein the stresses are the highest, close to the recess in the body 40 of the capsule. The polarization and the operation mode are similar to the case of FIG. 11a.

Figure 11C:
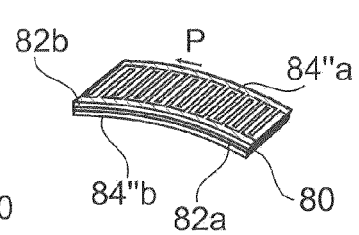

According to the embodiment of FIG. 11c, the piezoelectric component operates such that the polarization P is parallel to the stress, that is to say along the strip, because this is where the electromechanical coupling is the strongest. The electrodes 84"a, 84"b are then interdigitally shaped (e.g., arranged in an interleaved fashioned).

Figure 10A:
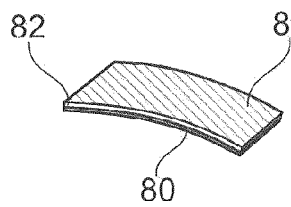
FIGS. 10a to 10c are perspective views of different electrode structures for unimorph piezoelectric strips, according to an exemplary embodiment.
Figure 10B:
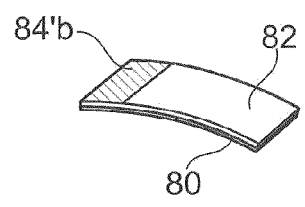
Figure 10C:
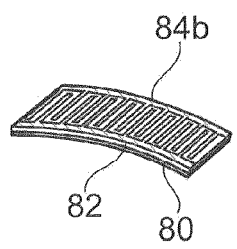

FIGS. 10a to 10c show component structures similar to those of FIGS. 11a to 11c, applied to components having only one unimorph piezoelectric layer 82 on one face of the substrate 80.

Figure 17A:
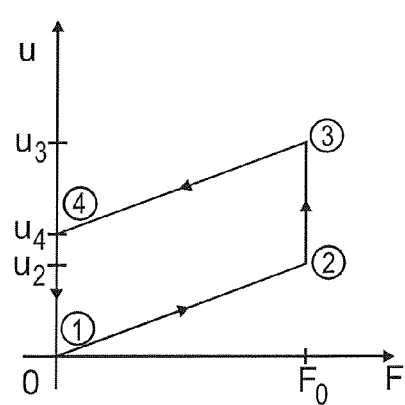
FIG. 17a is an exemplary diagram force F-movement u of the operating cycle of an implantable capsule, according to an exemplary embodiment.
Figure 17B:
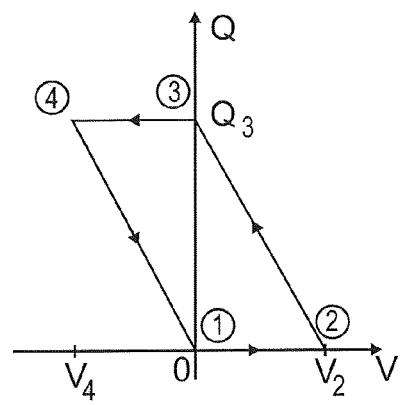
FIG. 17b is an example of diagram voltage V-load Q of the operating cycle of an implantable capsule, according to an exemplary embodiment.

An example of energy conversion cycle during which the force F applied to the transducer 50 passes from a null value to a maximum value $F_0$ will now be described with reference to FIGS. 17a and 17b.

Initially, in position ①, the system is at rest and all variables are equal to zero.

From position ① to position ②, the circuit is opened and the applied force F increases up to $F_0$.

During this phase, the charge Q is zero and the voltage V increases from 0 to $V_2$.

From position ② to position ③, under the force F0, the circuit is closed while harvesting the accumulated charges. In ③ we therefore have $Q=Q_3$. The circuit is then reopened.

From position ③ to position ④, the force F is reset to 0 and the load remains constant at $Q_3$. In ④, $V_4=-V_2$.

From position ④ to position ①, the circuit is closed while harvesting a second time the load.

The energy harvested per cycle is thus $W=V_2Q_3$.

Other conversion cycles are also possible, such as a cycle with a single charge extraction (passing directly from step ③ to step ①), or for example a cycle wherein the voltage is imposed across the piezoelectric layer to optimize the energy extraction.

Figure 9B:
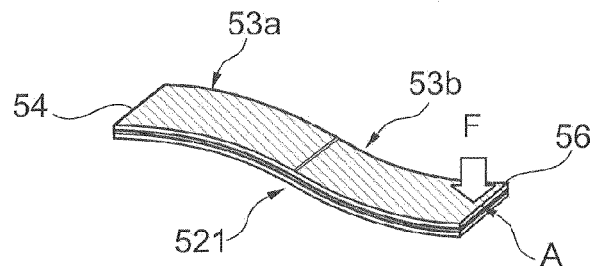

FIG. 9b illustrates another strip structure 521 with a simply recessed girder, formed by two strips 53a, 53b similar to the strip 53 of FIG. 9a, arranged in series and whose concavities are opposite in sign. The polarities developed by these strips being opposite, the electrodes of each of the strips are electrically isolated from each other.

Figure 6A:
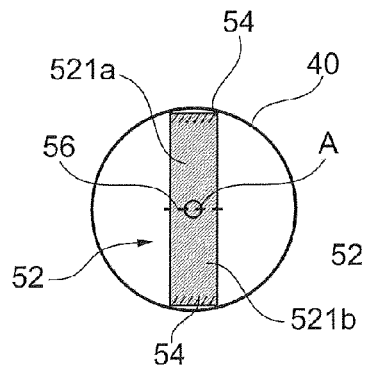
FIGS. 6a to 6c are top views of piezoelectric components made of straight strips, according to an exemplary embodiment.
Figure 9C:
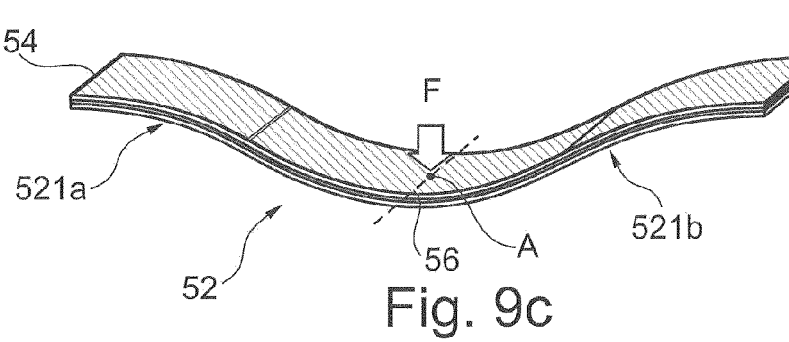

The component 52 of FIG. 6a is represented on FIG. 9c. This component 52 is shown as a double long girder resulting from the implementation of two parallel components 521a, 521b, which are each identical to the strip of FIG. 9b. Also in this case, the polarity inversion along the girder may be provided by electrical isolation of the electrodes according to their concavity.

FIGS. 6b through 8 show other piezoelectric components formed in various strip arrangements designed to extend the length of the piezoelectric structure without sacrificing compactness.

Figure 6B:
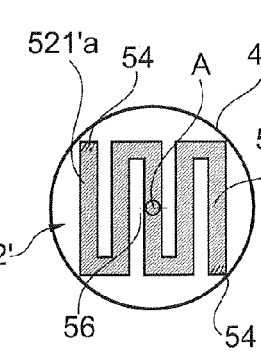
Figure 6C:
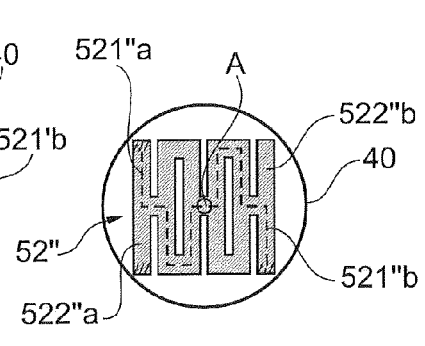

The strips of components 52', 52" of FIGS. 6b and 6c are formed of folded straight segments.

The piezoelectric component 52' of FIG. 6b includes two strips 521'a, 521'b disposed in parallel (yet having a different structure than the parallel strips 521a, 521b of FIG. 6a).

The piezoelectric component 52" of the FIG. 6c is more complex because it includes four strips 521"a, 521"b, 522"a, 522"b arranged in parallel pairs.

Figure 7A:
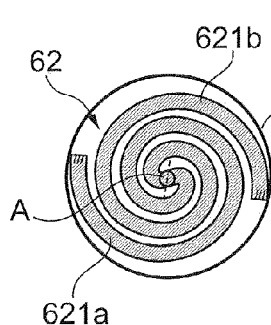
FIGS. 7a and 7b are top views of piezoelectric components made of spirally wounded strips, according to an exemplary embodiment.

The piezoelectric component 62 of FIG. 7a shows two bands 621a, 621b in parallel and coiled in spirals.

Figure 7B:
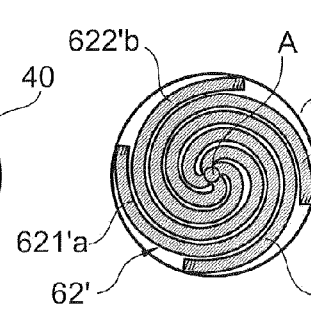

Similarly, the piezoelectric component 62' of FIG. 7b is a four-strip structure 621'a, 621'b, 622'a, 622'b spirally coiled forming two parallel components including, on the one hand, the strips 621'a, 621'b in parallel and, on the other hand, the strips 622'a, 622'b in parallel.

Figure 8:
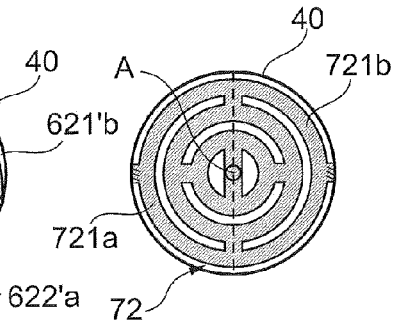
FIG. 8 is a top view of a piezoelectric component with an annular structure, according to an exemplary embodiment.

Finally, the component 72 of FIG. 8 is a circular beam formed by two annular band structures 721a, 721b in parallel.

In addition, it is advantageous in the case of a piezoelectric energy harvester to limit the mechanical stresses to have a reliable system over a large number of cycles, typically less than a few tens of MPa for a PZT type material, and to limit the voltage across the piezoelectric component to make it compatible with conventional electronic systems, that is to say less than 15 or 20 V.

Figure 13A:
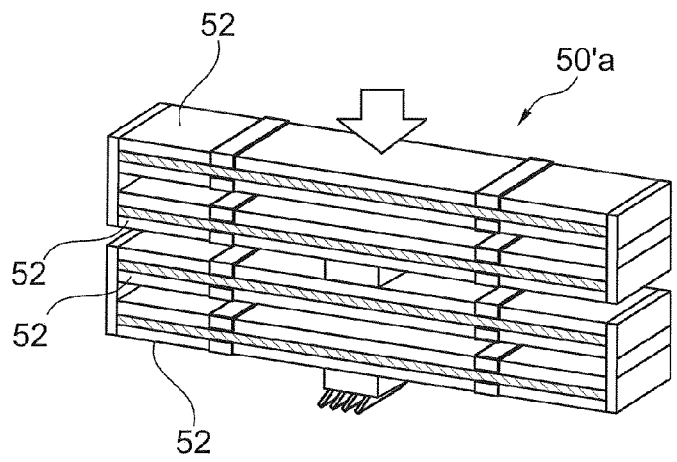
FIGS. 13a and 13b are perspective views showing piezoelectric transducers respectively made of straight piezoelectric components and of components coiled in series, according to an exemplary embodiment.
Figure 13B:
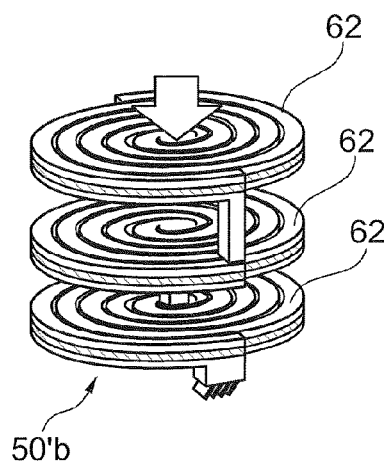

For this purpose, in some embodiments, the harvester transducers are arranging in series and in parallel and include several piezoelectric components arranged, for example, in a beam or a spiral. Indeed, for a mechanical energy input given by a force and displacement, transducers in series reduces the deformations of each element and reduces mechanical stress, and transducers in parallel reduces the thickness of the piezoelectric components to lower the voltage at constant electric field in the material. FIGS. 13a and 13b show transducers 50'a, 50'b having beam-type components 52 and spiral-type components 62, respectively, assembled in series.

Figure 14A:
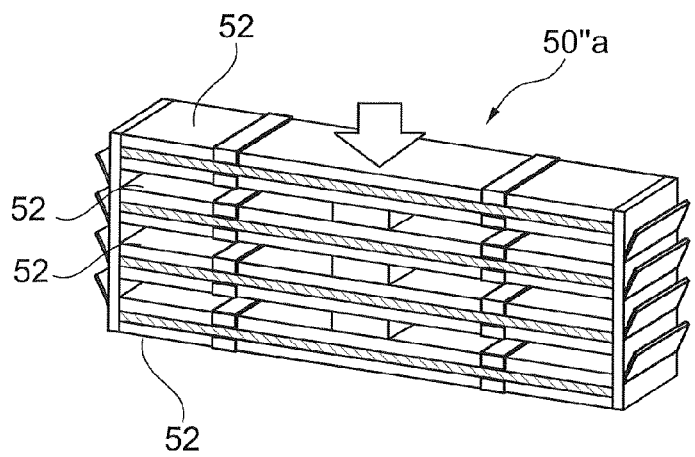
FIGS. 14a and 14b are perspective views showing piezoelectric transducers respectively made of straight piezoelectric components and of components coiled in parallel, according to an exemplary embodiment.
Figure 14B:
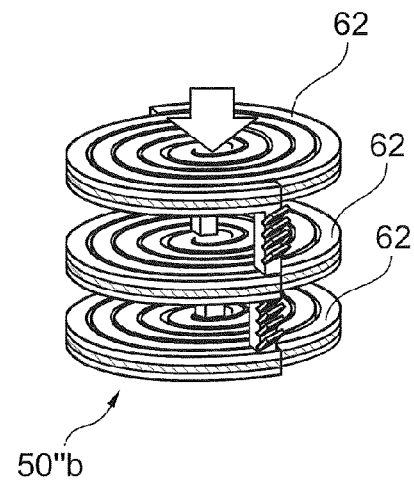

FIGS. 14a and 14b show transducers 50" and 50"b resulting from the parallel assembly of these same components 52, 62.

Figures 15, 16:
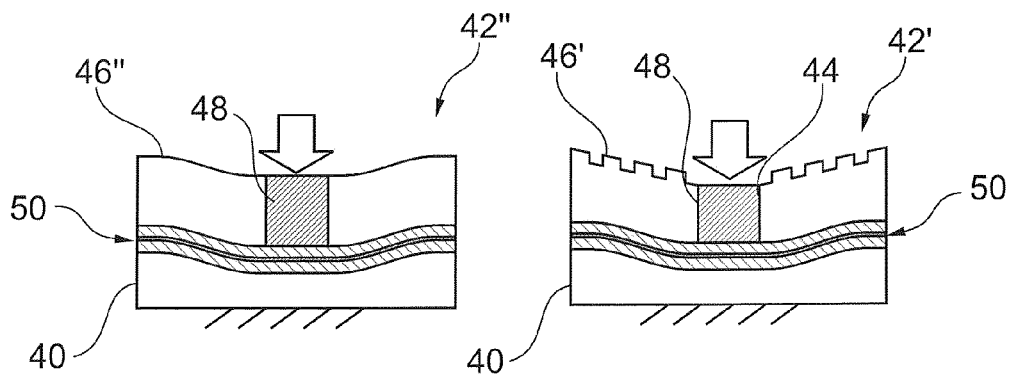
FIG. 15 is a sectional view of a first embodiment of the transducer of FIG. 5a, according to an exemplary embodiment.
FIG. 16 is a sectional view of a second embodiment of the transducer of FIG. 5a, according to an exemplary embodiment.

FIG. 15 shows a second embodiment of a capsule according to the invention, wherein the mobile actuator 42' comprises a planar rigid surface 44 coupled to the body 40 of the capsule by an elastically deformable element 46' for connection in the form of peripheral corrugations around the rigid surface 44.

FIG. 16 shows a third embodiment, with a mobile actuator 42" having a stretchable flexible membrane 46" attached to the body 40 of the capsule at its periphery and having at its center with the connecting rod 48 to the energy harvester transducer 50.

Referring generally to the Figures, an intracorporeal autonomous capsule is shown. The capsule includes a body 40 and, within the body, electronic circuitry 26-36 and an electrical power supply. The capsule includes a transducer 50 for energy harvesting, to convert a physical external solicitation F applied to the capsule in electrical quantity. The transducer 50 includes at least one piezoelectric component 52 coupled to a movable actuating member 42 for receiving said external physical solicitation. The piezoelectric component 52 can include at least one structure with at least one piezoelectric strip 521a, 521b fixed to the body 40 of the capsule at one end 54 and adapted to be subjected to an physical external solicitation F at an application point A located at another end 56. The capsule may further include an energy storage and management module 36 powered by the energy harvesting transducer 50 under the effect of deformation of the piezoelectric component 52 due to the external physical solicitation F transmitted by the mobile actuator element 42. The movable actuating member 42 may include a rigid surface 44 coupled to the piezoelectric component and a resiliently deformable bellows 46 for connection of the rigid surface of the rest of the body 40. The piezoelectric strip 521a, 521b may be of rectilinear form. The piezoelectric strip 621a, 621b may be spirally wound. The piezoelectric strip 521'a, 521'b may be formed of folded rectilinear segments. The piezoelectric strip 721a, 721b may include an annular structure. The piezoelectric component 52, 52', 62 may include two piezoelectric strips in parallel around a common application point A. The piezoelectric component 52", 62' has a plurality of strip structures arranged in parallel. The energy harvesting transducer 50'a, 50'b may include a plurality of piezoelectric members 52, 62 arranged in series. The energy harvesting transducer 50"a, 50"b may include a plurality of piezoelectric members 52, 62 arranged in parallel. The piezoelectric strip 521a, 521b may be formed of a substrate 80, with at least one layer of piezoelectric material 82a, 82b deposited on one face of the substrate and at least one electrode 84a, 84b at least partially covering the layer of piezoelectric material. A layer 82 of piezoelectric material may be deposited on one face of the substrate 80. A layer 82a, 82b of piezoelectric material may be deposited on each side of the substrate 80. An electrode 84, 84a, 84b may completely covers the layer 82, 82a, 82b of piezoelectric material. The at least one electrode 84', 84'a, 84'b may partly cover the layer 82, 82a, 82b of piezoelectric material. The electrodes 84", 84"a, 84"b covering the layer 82, 82a, 82b of piezoelectric material are staggered.

This capsule includes a body 40 and, within the body, electronic circuitry and power supply methods including of: a transducer for energy harvesting, to convert a physical external stress F applied to the capsule in electrical quantity, this transducer including at least one piezoelectric component 50 coupled to a mobile actuator element 42 in the form of a resiliently deformable bellows 46 receiving the external physical stress, with a rigid surface 44 coupled to the piezoelectric component; and a module for storing and managing energy, supplied by the energy harvesting transducer as a result of a deformation of the piezoelectric component due to the external physical stress F transmitted by the mobile actuator 42. The power supply methods are devoid of seismic mass and the piezoelectric component 50 has at least one structure with at least one piezoelectric strip attached to the body of the capsule at one end and able of being subjected to physical external stress in an application point located at another end (FIG. 5b).

What is claimed is:

1. An intracorporeal autonomous capsule, comprising:
   a body enclosing electronic circuitry including a power supply;
   a transducer to convert an external force applied to the capsule into electric potential, the transducer comprising at least two piezoelectric strips arranged in series and having concave portions opposite in polarity, wherein the at least two piezoelectric strips arranged in series comprise a first side and a second side, wherein the first side of the piezoelectric strips are coupled to a movable actuating member having a rigid surface which directly receives said external force and which is coupled to the first side of the piezoelectric strips, and wherein the second side of the piezoelectric strips are fixed to the body of the capsule; and
   an energy storage and management module powered by the transducer under the effect of deformation of the piezoelectric strips due to the external force.

2. The capsule of claim 1, further comprising:
   a resiliently deformable bellows connecting the rigid surface to the body.

3. The capsule of claim 1, wherein the piezoelectric strip form a thin beam spanning a cross-sectional area of the body without covering the entirety of the cross-sectional area.

4. The capsule of claim 1, wherein the piezoelectric strips are formed of folded rectilinear segments.

5. The capsule of claim 4, wherein the capsule includes a circular cross-sectional area and wherein the piezoelectric strips are rectilinear, and wherein the rectilinear piezoelectric strips span the center axis of the circular cross-sectional area.

6. The capsule of claim 5, wherein a connecting post is coupled between the rigid surface of the movable actuating member and the rectilinear piezoelectric strips near the center axis of the circular cross-sectional area.

7. The capsule of claim 1, wherein the piezoelectric strips are spirally wound and wherein a face of the spiral spans a cross-sectional area of the body without covering the entirety of the cross-sectional area.

8. The capsule of claim 1, wherein the piezoelectric strips have a circular structure with at least one aperture such that a face of the strip spans a cross-sectional area of the body without covering the entirety of the cross-sectional area.

9. The capsule of claim 1, wherein the energy harvesting transducer comprises a plurality of piezoelectric members arranged in series along the piezoelectric strips.

10. The capsule of claim 1, wherein the piezoelectric strips are formed of a substrate with at least one layer of piezoelectric material deposited on one face of the substrate and at least one electrode at least partially covering the layer of piezoelectric material.

11. The capsule of claim 10, wherein a layer of piezoelectric material is deposited on one face of the substrate.

12. The capsule of claim 10, wherein a layer of piezoelectric material is deposited on each side of the substrate.

13. The capsule of claim 10, wherein the electrode completely covers the layer of piezoelectric material.

14. The capsule of claim 10, wherein the at least one electrode partly covers the layer of piezoelectric material.

15. The capsule of claim 10, wherein a plurality of electrodes cover the layer of piezoelectric material, and wherein the plurality of electrodes are interleaved.

16. The capsule of claim 1, wherein the body is configured to be engaged with only one human tissue when installed and the rigid surface is not directly coupled to any human tissue, and wherein the body is configured to be engaged with the myocardial wall of a heart by a flexible fastener but the body otherwise floats freely in the cavity of the heart, wherein blood pressure changes due to the beating of the heart cause mechanical cycling of the rigid surface despite opposite force by the piezoelectric strips, and wherein the power supply circuit is configured to harvest energy, using the piezoelectric strips, according to the beats of the heart.

* * * * *